United States Patent
Haruna et al.

(10) Patent No.: US 10,813,654 B2
(45) Date of Patent: Oct. 27, 2020

(54) NOSE KNIFE

(71) Applicant: MANI, Inc., Utsunomiya-shi, Tochigi (JP)

(72) Inventors: Shinichi Haruna, Shimotsuga-gun (JP); Masato Suda, Utsunomiya (JP); Masaaki Matsutani, Utsunomiya (JP)

(73) Assignee: MANI, INC., Utsunomiya-shi, Tochigi (JP)

( * ) Notice: Subject to any disclaimer, the term of this patent is extended or adjusted under 35 U.S.C. 154(b) by 0 days.

(21) Appl. No.: 16/341,431

(22) PCT Filed: Oct. 11, 2017

(86) PCT No.: PCT/JP2017/036786
§ 371 (c)(1),
(2) Date: Apr. 11, 2019

(87) PCT Pub. No.: WO2018/070409
PCT Pub. Date: Apr. 19, 2018

(65) Prior Publication Data
US 2019/0262017 A1    Aug. 29, 2019

(30) Foreign Application Priority Data
Oct. 13, 2016   (JP) .................... 2016-201636

(51) Int. Cl.
*A61B 17/24*        (2006.01)
*A61B 17/3211*    (2006.01)
*A61B 17/32*        (2006.01)

(52) U.S. Cl.
CPC .............. *A61B 17/24* (2013.01); *A61B 17/32* (2013.01); *A61B 17/3211* (2013.01)

(58) Field of Classification Search
CPC ................ A61B 17/24; A61B 17/3211; A61B 17/320016; A61B 17/32
See application file for complete search history.

(56) References Cited

U.S. PATENT DOCUMENTS 1,339,691 A  *  5/1920  Diamant ................ A61B 17/24
                                                                606/110
1,628,275 A  *  5/1927  Robinson .............. A61F 11/006
                                                                606/161
(Continued)

FOREIGN PATENT DOCUMENTS

JP        S60128611 U1    8/1985
JP        H04067414 U1    6/1992
(Continued)

OTHER PUBLICATIONS

Review_of_Computer-Aided_Sinus_Surgery, Byung-Ju Yi, Hyun-Soo Yoon, Hanyang Medical Rev 2016;36:248-253.*
(Continued)

*Primary Examiner* — Sean M Michalski
(74) *Attorney, Agent, or Firm* — Isshiki International Law Office; Joseph P. Farrar, Esq.

(57) ABSTRACT

A nose knife with good usability and little interference with tools such as an endoscope in nasal cavity surgery is provided, and includes a handle, a shank, and a blade. The shank includes a straight part connected straight to the handle along the same axis, and a curved part integrally connected to the front end of the straight part. The blade is provided at the front end of the curved part. A tip of the blade is angled 65 degrees to 75 degrees inclusive relative to the axis of the straight part.

4 Claims, 3 Drawing Sheets

(56) References Cited

U.S. PATENT DOCUMENTS

| | | | | |
|---|---|---|---|---|
| 3,256,874 A * | 6/1966 | De Marco | A61B 10/0291 | 600/564 |
| 4,572,180 A * | 2/1986 | Deenadayalu | A61B 1/227 | 600/249 |
| 5,152,744 A * | 10/1992 | Krause | A61B 17/32002 | 604/22 |
| 5,203,865 A * | 4/1993 | Siepser | A61B 17/3211 | 30/162 |
| 5,217,476 A * | 6/1993 | Wishinsky | A61B 17/3211 | 128/898 |
| 5,234,452 A * | 8/1993 | Wang-On | A61B 17/50 | 606/160 |
| 5,282,796 A * | 2/1994 | Knoepfler | A61B 17/320016 | 604/264 |
| 5,282,816 A * | 2/1994 | Miller | A61B 17/1659 | 606/167 |
| 5,320,635 A * | 6/1994 | Smith | A61B 17/32002 | 408/713 |
| 5,336,235 A * | 8/1994 | Myers | A61F 9/0133 | 606/166 |
| 5,522,829 A * | 6/1996 | Michalos | A61B 17/32001 | 433/102 |
| 5,876,416 A * | 3/1999 | Hill | A61B 17/32 | 30/186 |
| 5,893,861 A * | 4/1999 | Yumoto | A61B 17/320036 | 606/167 |
| D423,669 S * | 4/2000 | Huttner | D24/147 | |
| D428,489 S * | 7/2000 | Huttner | D24/147 | |
| 7,055,248 B2 * | 6/2006 | Cote | A61B 17/3213 | 30/337 |
| 7,331,956 B2 * | 2/2008 | Hovda | A01N 43/52 | 606/32 |
| 10,238,417 B1 * | 3/2019 | Carpenter | A61B 17/320708 | |
| 2001/0029386 A1 * | 10/2001 | Matsutani | A61F 9/0133 | 606/166 |
| 2003/0074014 A1 * | 4/2003 | Castaneda | A61B 17/320016 | 606/167 |
| 2004/0024401 A1 * | 2/2004 | Garito | A61B 18/1402 | 606/45 |
| 2004/0089159 A1 * | 5/2004 | Matsutani | A61B 17/3211 | 99/339 |
| 2004/0133224 A1 * | 7/2004 | Scheller | A61F 9/0133 | 606/166 |
| 2004/0153108 A1 * | 8/2004 | Matsutani | A61B 17/3211 | 606/159 |
| 2004/0243157 A1 * | 12/2004 | Connor | A61B 17/320016 | 606/159 |
| 2004/0260276 A1 * | 12/2004 | Rudko | A61B 18/24 | 606/15 |
| 2006/0029906 A1 * | 2/2006 | Hill | A61C 3/00 | 433/141 |
| 2006/0058824 A1 * | 3/2006 | Kozlowski | A61B 17/3211 | 606/167 |
| 2006/0263745 A1 * | 11/2006 | Lasner | A61C 3/14 | 433/144 |
| 2006/0276816 A1 * | 12/2006 | Eckman | A61B 17/320708 | 606/160 |
| 2007/0073282 A1 * | 3/2007 | McGaffigan | A61B 18/082 | 606/29 |
| 2007/0129751 A1 * | 6/2007 | Muni | A61M 31/005 | 606/196 |
| 2008/0065222 A1 * | 3/2008 | Hamada | A61F 2/4465 | 623/17.16 |
| 2008/0269791 A1 * | 10/2008 | Hoenes | A61B 5/15146 | 606/181 |
| 2013/0066164 A1 * | 3/2013 | Nakamura | A61B 17/22031 | 600/247 |
| 2015/0018714 A1 * | 1/2015 | Chen | A61B 10/0291 | 600/570 |
| 2016/0030368 A1 * | 2/2016 | Atkins, Jr. | A61M 5/002 | 514/537 |
| 2017/0014152 A1 * | 1/2017 | Noui | A61B 17/24 | |
| 2017/0164975 A1 * | 6/2017 | Wu | A61B 17/320708 | |

FOREIGN PATENT DOCUMENTS

| | | |
|---|---|---|
| JP | 2004147914 A | 5/2004 |
| JP | 2006006692 A | 1/2006 |
| JP | 2009511097 A | 3/2009 |
| WO | 2012074084 A1 | 6/2012 |
| WO | 2015132401 A1 | 9/2015 |

OTHER PUBLICATIONS

International Search Report (ISR) for Application No. PCT/JP2017/036786 dated Nov. 7, 2017.

Translation of the ISR for Application No. PCT/JP2017/036786 dated Nov. 7, 2017.

Written Opinion of the International Search Authority for Application No. PCT/JP2017/036786 dated Nov. 7, 2017.

* cited by examiner (a)

(b)

NOSE KNIFE

CROSS REFERENCE TO RELATED APPLICATIONS

The present application is a national phase entry under 35 U.S.C. § 371 of International Application No. PCT/JP2017/036786, filed Oct. 11, 2017, which claims priority from Japanese Application No. JP2016-201636, filed Oct. 13, 2016, the entire disclosures of which are hereby incorporated by reference herein.

TECHNICAL FIELD

The present invention relates to a nose knife used in nasal cavity surgery.

BACKGROUND ART

A dedicated nose knife is used in surgery for nasal cavity diseases. FIG. 4 shows diagrams (a) and (b) exemplifying conventionally used nose knives.

A nose knife 100 in FIG. 4(a) includes a linear shank 11 having a cross-sectional circular shape, a handle 13 applied with a non-slip surface on the base end side of the shank 11, and a blade 12 on the front end side. The diameter of the cross-section of the shank 11 is approximately 3 mm, and length from the base end side of the shank 11 to the blade tip of the blade 12 is approximately 55 mm. The blade 12 is formed protruding slightly from the front end side of the shank 11 and bending from there at nearly a right angle.

A nose knife 101 of FIG. 4(b) includes a shank 11 having a cross-sectional shape of an approximately 2 mm×4 mm rectangle. Length from the base end side of the shank 11 to the blade tip of the blade 12 is approximately 43 mm. The shank 11 has a linear shape, and a cross-section decreasing from the middle toward the blade 12. Note that while it is difficult to use the nose knife 101 while rotating it around the axis since the cross-section of the shank 11 is approximately rectangular, it does not slip easily and incisions, etc., may be surely made.

In the case of nasal cavity surgery, the nose knife is inserted in a nostril, and incising and sampling and paring body tissue off, etc., are carried out. At this time, since the nasal cavity is narrow and the interior is difficult to see, an endoscope is often inserted in the nostril at the same time as the nose knife is done in the same way so as to provide treatment in recent years. Here, in the case of the nose knives 100 and 101 as illustrated in FIG. 4(a) and FIG. 4(b), since the shank 11 is thick and has a short length, the handle 13 touches the endoscope, whereby the endoscope and the nose knife interfere with each other. Therefore, a thinner and longer shank of the nose knife is preferred when considering only usability. However, since there are cases where a relatively large force is applied when sampling body tissue, etc., the shank requires a certain amount of strength. That is, the shape of the shank should be determined taking usability and strength into account.

Moreover, an angle between the handle and the blade needs to be given attention as well in order to improve usability of the nose knife. In Patent Document 1 (JP 2004-147914A), for example, curved parts are provided in two places from the handle to the blade tip so as to improve visibility of the knife during surgery, and to make the angle of the knife main body at which it touches a blood vessel be diversely variable.

PRIOR ART DOCUMENTS

Patent Documents

[Patent Document 1] JP 2004-147914A

DISCLOSURE OF THE INVENTION

Problem to be Solved by the Invention

In light of the problem, the present invention aims to provide a nose knife with good usability and little interference with tools such as an endoscope.

Solution to the Problem

The nose knife of the present invention for solving the above problem includes a handle, a shank, and a blade. The shank is characterized in that it includes a straight part connected straight to the handle along the same axis of the handle, and a curved part integrally connected to the front end of the straight part, and the blade is provided at the front end of the curved part, and direction of a blade tip of the blade is 65 degrees to 75 degrees inclusive to the axis line of the straight part.

Moreover, length of the straight part is 50 mm to 60 mm inclusive, and the blade tip of the blade may be located 10 mm to 20 mm inclusive from the central axial line of the straight part in a perpendicular direction to the central axial line. Furthermore, cross-sectional shape of the straight part may be a circle having a diameter of 1.5 mm to 2.5 mm inclusive.

Advantageous Effect of the Invention

According to the nose knife of the present invention, usability of the nose knife in surgery may be improved by providing a curved part and providing a blade at a desired angle.

Furthermore, since the blade tip of the blade is only a desired distance from the straight part, the incision range when the handle is rotated may be enlarged. Moreover, making the cross-sectional shape of the straight part be a circle with a small diameter allows reduction in interference with tools such as an endoscope, thereby improving usability.

DESCRIPTION OF EMBODIMENTS

An embodiment according to the present invention is described below with reference to the accompanying drawings.

Figure 1:
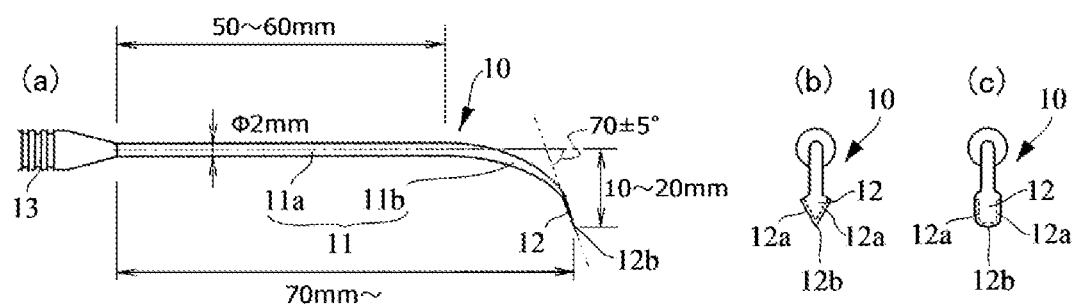
FIG. 1 shows diagrams for describing a nose knife of the present invention, wherein (a) is a side view thereof, (b) is a front view thereof, and (c) is a front view of a different blade form.

FIG. 1 shows diagrams for describing a nose knife of the present invention, wherein FIG. 1(a) is a side view thereof, FIG. 1(b) is a front view thereof, and FIG. 1(c) is a front view of a different blade form. A general structure of this nose knife 10 includes a handle 13, a shank 11, and a blade 12.

The handle 13 is a part for a surgeon to grasp during nasal cavity surgery, and is often subjected to non-slip processing. Note that the structure of a non-slip surface is not particularly limited since there are various non-slip processing methods. Moreover, since the nose knife 10 may be rotated around the axis of the handle 13 so as to make an incision, it is good that the cross-section of the handle 13 has a circular shape.

The shank 11 is made up of a straight part 11a connected straight to the handle 13 along the same axis thereof, and a curved part 11b integrally connected to the front end of the straight part 11a. Length of the straight part 11a is preferably 50 to 60 mm, and the entire length of the curved part 11b and the blade 12 added thereto is 70 mm or greater. There is a merit that the longer the length of the shank 11, the further into the nasal cavity the blade 12 reaches; however, if it is too long, usability is degraded, and therefore the resulting optimal length of the straight part 11a is 50 to 60 mm. Note that this length is long enough for the nose knife, allowing it to be used to incise and pare off portions that could not be reached in the past.

The cross-sectional shape of the straight part 11a is preferably a circle with a basic diameter of 2.0 mm within the range of 1.5 to 2.5 mm. This size of the straight part 11a has a small cross section, thereby allowing reduction in mutual interference between the nose knife and the endoscope when they are inserted into a nostril. However, a problem of strength occurs if it is too narrow, and thus the smallest value of the diameter is set to 1.5 mm.

While both of the blades 12 illustrated in FIGS. 1(b) and 1(c) are connected integrally to the front end of the curved part 11b, the blade 12 illustrated in FIG. 1(b) is provided with cutting edges 12a in two directions from a pointed end, and the blade 12 illustrated in FIG. 1(c) is provided with U-shaped cutting edges 12a. In this case, for the pointed cutting edges 12a, a blade tip 12b is a pointed end of the cutting edges 12a, and for the U-shaped cutting edges 12a, it indicates a location farthest from front ends of the curved part 11b at the bottom side of the U. The shape of the blade 12 itself is not particularly limited and may be either one of FIGS. 1(b) and 1(c); however, assuming that the blade tip 12b passes first through body tissue to make an incision, etc., it is preferred that the direction of the blade tip 12b of the blade 12 should be at an angle of approximately 70 degrees plus or minus 5 degrees to the axis direction of the straight part 11a. However, the angle may be set to approximately 90 degrees according to conditions such as location of incision or paring off.

Figure 2:
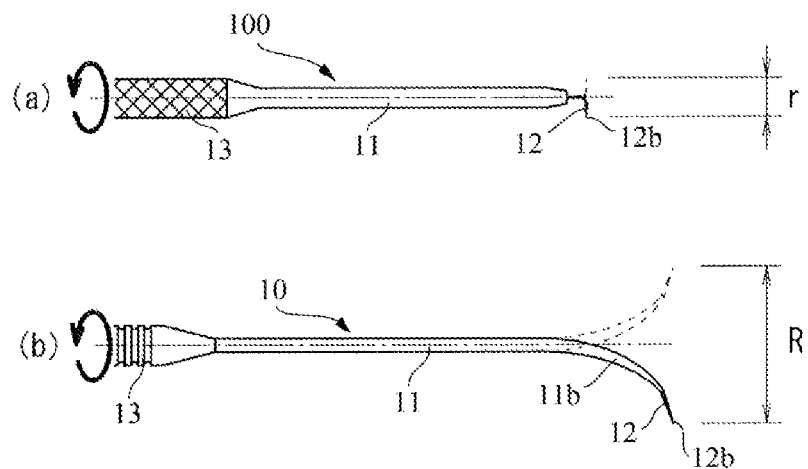
FIG. 2 shows diagrams comparing incision ranges of nose knives, wherein (a) is a conventional nose knife and (b) is the nose knife of the present invention.

Moreover, the blade tip 12b is located 10 to 20 mm away from the central axial line of the straight part 11a in a perpendicular direction. FIG. 2 shows diagrams comparing incision ranges of nose knives, wherein FIG. 2(a) is a conventional nose knife and FIG. 2(b) is the nose knife of the present invention. The diagrams illustrate ranges for incising, etc., when the respective nose knives 100 and 10 are rotated around the axis. While the blade 12 can only be moved within a range r with the conventional nose knife 100, the blade 12 can be moved within a larger range R than the range r with the nose knife 10 having the curved part 11b according to the present invention. In other words, even with the same rotating angle, the nose knife 10 of the present invention may achieve a larger incision range. Note that the incision range is larger as distance from the central axial line of the straight part 11a to the blade tip 12b is larger, but if it is too large, usability of the nose knife 10 is degraded, and curving of the curved part 11b is increased, thereby leading to a problem of strength.

In this case, the distance from the central axial line of the straight part 11a to the blade tip 12b is determined by the bending shape of the curved part 11b and the angle of the blade 12. In the case where an endoscope is not used, shape of the curved part 11b and angle of the blade 12 need to be determined taking into consideration visual performance of the blade 12 during surgery, as with conventional technology.

In this manner, a conclusion has been made that with consideration of balance between incision range and usability, etc., location of the blade tip 12b is preferably within a range of 10 to 20 mm in a perpendicular direction from the central axial line of the straight part 11a, and the angle of the blade 12 is optimally approximately 70 degrees plus or minus 5 degrees to the axis direction of the straight part 11a.

Figure 3:
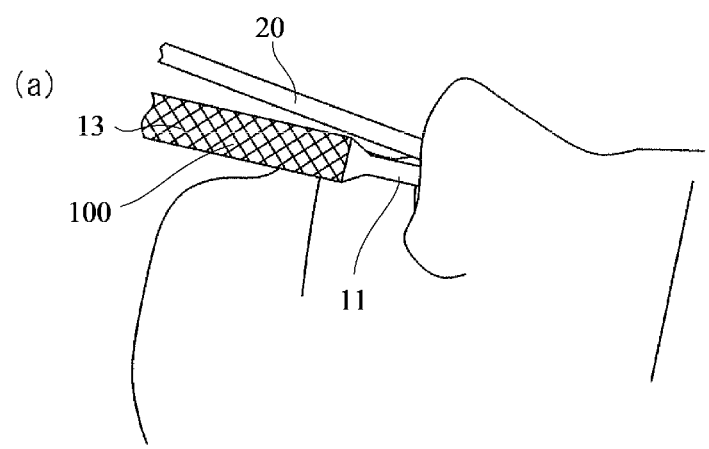
FIG. 3 shows diagrams describing states where an endoscope and a nose knife are inserted in a nostril, wherein (a) is a conventional nose knife and (b) is the nose knife of the present invention.
Figure 3:
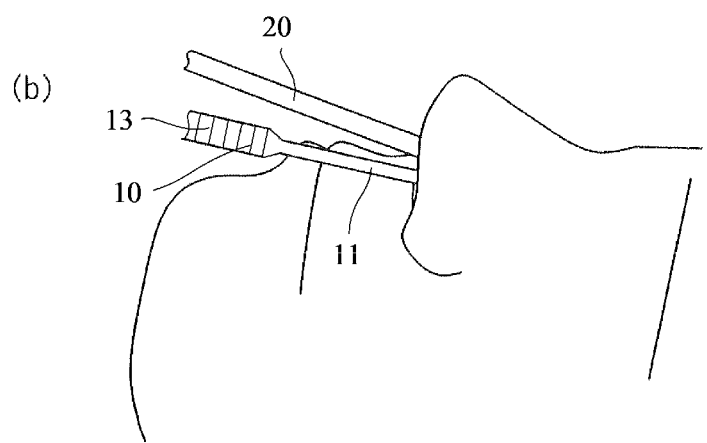
Figure 4:
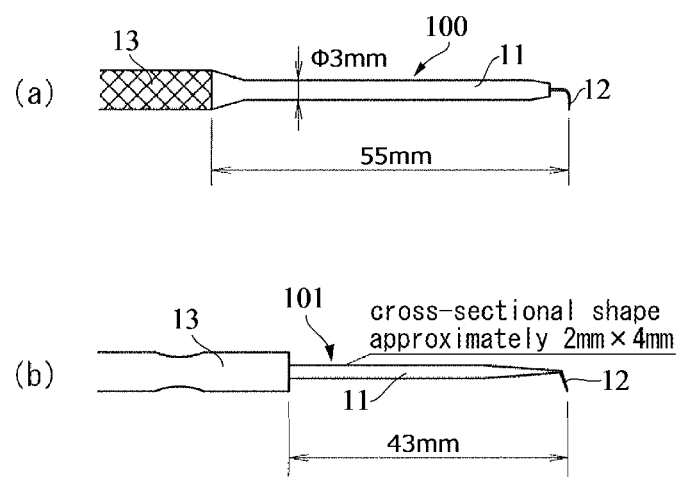
FIG. 4 shows diagrams exemplifying conventionally used nose knives (a) and (b).

The diameter of the shank 11 of the conventional nose knife is typically approximately 3.0 mm, which is determined so as to ensure flexural capacity because relatively large force is applied when the body tissue of the nasal cavity, etc., are sampled. However, use of an endoscope for nasal cavity surgery has increased in recent years, where in that case, both the nose knife and the endoscope are inserted in the nostril. FIG. 3 shows diagrams describing states where an endoscope and a nose knife are inserted in a nostril, wherein FIG. 3(a) is a conventional nose knife and FIG. 3(b) is the nose knife of the present invention.

Naturally, when both the nose knife 10 and the endoscope 20 are inserted in a nostril, a smaller diameter of the shank 11 of the nose knife 10 is preferred since interference with the endoscope 20 is reduced. Moreover, since the handle 13 typically has a larger cross-section than that of the shank 11, interference between the handle 13 and the endoscope 20 also requires attention. Taking this into consideration, making the shank 11 of the nose knife 10 of the present invention narrower and longer than that of the conventional nose knife 100 reduces interference between the handle 13 and the endoscope 20.

As described above, the nose knife of the present invention has excellent usability, little interference with an endoscope, and secures sufficient strength, thereby providing excellent beneficial effects.

EXPLANATION OF REFERENCE NUMERALS

10: Nose knife
11: Shank
11a: Straight part
11b: Curved part
12: Blade
12a: Cutting edge
12b: Blade tip
13: Handle
20: Endoscope

The invention claimed is:
1. A nose knife comprising:
a handle having a non-slip surface and a circular cross-section;
a shank including a single straight part, extending the length of the shank, connected to the handle and aligned with a main longitudinal axis of the handle, and a curved part integrally connected to a front end of the straight part; and a blade with a cutting edge, provided at a front end of the curved part of the shank, wherein a tip of the blade is angled 65 degrees to 75 degrees inclusive relative to a central axis of the straight part of the shank, wherein the nose knife is configured to be rotated around the longitudinal axis of the handle so as to make an incision.

2. The nose knife of claim 1, wherein a length of the straight part is 50 mm to 60 mm inclusive, and the tip of the blade is located 10 mm to 20 mm inclusive from the central axis of the straight part in a perpendicular direction to the central axis.

3. The nose knife of claim 1, wherein a cross-sectional shape of the straight part is a circle having a diameter of 1.5 mm to 2.5 mm inclusive.

4. The nose knife of claim 2, wherein a cross-sectional shape of the straight part is a circle having a diameter of 1.5 mm to 2.5 mm inclusive.

\* \* \* \* \*